United States Patent [19]
Parkola

[11] Patent Number: 5,417,707
[45] Date of Patent: May 23, 1995

[54] DILATATION BALLOON PROTECTOR WITH RAISED RIBS

[75] Inventor: Walter R. Parkola, El Cajon, Calif.

[73] Assignee: Medtronic, Inc., Minneapolis, Minn.

[21] Appl. No.: 145,895

[22] Filed: Oct. 29, 1993

[51] Int. Cl.⁶ .............................................. A61M 25/00
[52] U.S. Cl. ...................................... 606/194; 604/96
[58] Field of Search ............... 606/194, 198; 206/438; 604/96

[56] References Cited

U.S. PATENT DOCUMENTS

| | | | |
|---|---|---|---|
| 3,788,318 | 1/1974 | Kim et al. | 606/198 X |
| 5,181,913 | 1/1993 | Erlich | 206/438 X |
| 5,192,307 | 3/1993 | Wall | 606/194 X |
| 5,279,573 | 1/1994 | Klosterman | 206/438 X |

Primary Examiner—Stephen C. Pellegrino
Assistant Examiner—Nancy Mulcare
Attorney, Agent, or Firm—Dianne M. F. Plunkett; Harold R. Patton

[57] ABSTRACT

A one-piece balloon protector apparatus for a dilatation catheter. The disclosed protector comprises a unitary, planar element having two sets of longitudinal ribs, one set being disposed on a first planar face of the protector along a first edge and another set being disposed on the opposite planar face of the protector on the opposite edge. The protector is installed around a dilatation catheter balloon by placing the balloon on the protector and then coiling or wrapping the protector around the balloon. The two sets of ribs thus come come into contact an interlock with one another to secure the protector in a cylindrical configuration around the balloon.

8 Claims, 3 Drawing Sheets

DILATATION BALLOON PROTECTOR WITH RAISED RIBS

FIELD OF THE INVENTION

This invention relates to the field of angioplasty, and more particularly to a balloon protector of a dilatation balloon catheter.

BACKGROUND OF THE INVENTION

Angioplasty has become widely accepted as an efficient and effective method for opening stenoses in the coronary arteries and in other parts of the vascular system. The most widely used form of angioplasty makes use of a dilatation catheter which has an inflatable balloon at its distal end. Using fluoroscopy, the physician guides the catheter through the vascular system until the balloon is positioned across the stenosis. The balloon is then inflated by supplying a fluid under pressure through an inflation lumen to the balloon. The inflation of the balloon causes stretching of the artery and pressing of the lesion into the artery wall to reestablish acceptable blood flow through the artery.

One important characteristic of a dilatation catheter used for angioplasty is its profile, i.e., the outer diameter of the distal end portion of the balloon. Considerable effort has been spent in developing low-profile dilatation balloon catheters by minimizing the dimensions of the core or inner tube which extends through the balloon to its distal end, and by reducing wall thicknesses, to the extent possible, of the balloon itself.

Another important consideration is the outer diameter of the catheter in its deflated condition. This outer diameter affects the ease and ability of the dilatation catheter to pass through a guide catheter and through the coronary arteries leading to the stenosis to be opened.

In order to reduce the outer diameter of the balloon catheter in its deflated condition, it is common to fold or wrap the flaps of the deflated balloon. When inflation fluid is applied to the deflated balloon, it causes the balloon flaps to unwrap so that the balloon can inflate to its fully inflated condition.

In the prior art, it has been common to use a balloon protector in conjunction with a balloon dilatation catheter. A balloon protector serves at least two important functions. First, it protects the balloon and distal tip of the catheter from possible damage during shipping. Second, the balloon protector keeps the balloon tightly wrapped in its deflated condition to minimize the outer diameter of the balloon in its deflated state.

A balloon protector is typically applied to the distal end portion of the catheter prior to sterilization of the catheter. The sterilization process can involve exposing the catheter, with the balloon protector in place, to an elevated temperature for a period of time.

With certain balloon materials, the sterilization process will advantageously cause the balloon to be heat set in the folded or wrapped configuration in which it is held by the balloon protector. As a result, when the balloon protector is later removed, the balloon remains in this tightly wrapped or folded configuration. The heat setting of a balloon has the further advantage that when the balloon is inflated and then deflated, as it may be several times during an angioplasty procedure, the application of negative pressure during deflation will cause the balloon to return to its tightly wrapped heat set configuration. This greatly facilitates the removal of the catheter after the procedure has been performed.

Various types and configurations of balloon protectors have been shown in the prior art, for example, in U.S. Pat. Nos. 4,738,666 and 4,710,181 to Fuqua, in U.S. Pat. No. 5,053,007 to Euteneuer, U.S. Pat. No. 5,066,298 to Hess, and U.S. Pat. No. 4,573,981 to McFarlane.

The above-noted Fuqua '666 and '181 patents propose a catheter protector comprising a hollow cylindrical sheath. The Fuqua sheath covers the entire length of the catheter, and is removed by pulling it off of the proximal end of the catheter. Fuqua also proposes providing perforations in the sheath for facilitating its removal.

The above-noted Euteneuer '007 patent proposes a compression protector employing an inner sleeve applied over a deflated balloon, an outer sleeve applied over the inner sleeve, and a compression housing for compressing the outer sleeve radially in on the inner sleeve, thus compressing the inner sleeve radially in on the balloon.

The above-noted Hess '298 patent proposes protecting a catheter's balloon by wrapping the balloon with tape in an overlapping fashion.

The above-noted McFarlane '981 patent proposes a substantially tapered cylindrical sheath which encloses a distal portion of the catheter assembly.

As catheter distal sections, including catheter balloons, have become smaller, thinner, and more fragile, it has become increasingly difficult to apply a balloon protector which does not damage the catheter or the balloon and yet wraps the balloon as tightly as possible. Thus, there is perceived by the inventor to be a continuing need for improved balloon protectors for dilatation balloon catheters.

SUMMARY OF THE INVENTION

Accordingly, the present invention is directed to an improved balloon protector for covering and protecting the balloon of a dilatation catheter.

In accordance with one aspect of the invention, a balloon protector is provided which can be installed without the need to slide the protector over the balloon and risk damage to the balloon.

In accordance with another aspect of the present invention, a balloon protector is provided which can be readily removed from the balloon prior to use, similarly without the need for sliding the protector over the balloon and without the need for cutting or tearing the protector.

In one embodiment, the present invention comprises a unitary, substantially planar element having two sets of angular, longitudinal ribs disposed thereon. The two sets are disposed on opposite planar faces and on opposite ends of the planar element, such that when the planar element is coiled into a substantially cylindrical configuration, the two sets of ribs come into contact and interlock with one another. The interlocking of the ribs holds the planar element in its cylindrical configuration.

BRIEF DESCRIPTION OF THE DRAWINGS

The foregoing and other features of the present invention will be best appreciated with reference to the following detailed description of a specific embodiment of the invention, when read in conjunction with the accompanying drawings, wherein.

DETAILED DESCRIPTION OF A SPECIFIC EMBODIMENT OF THE INVENTION

Figure 1:
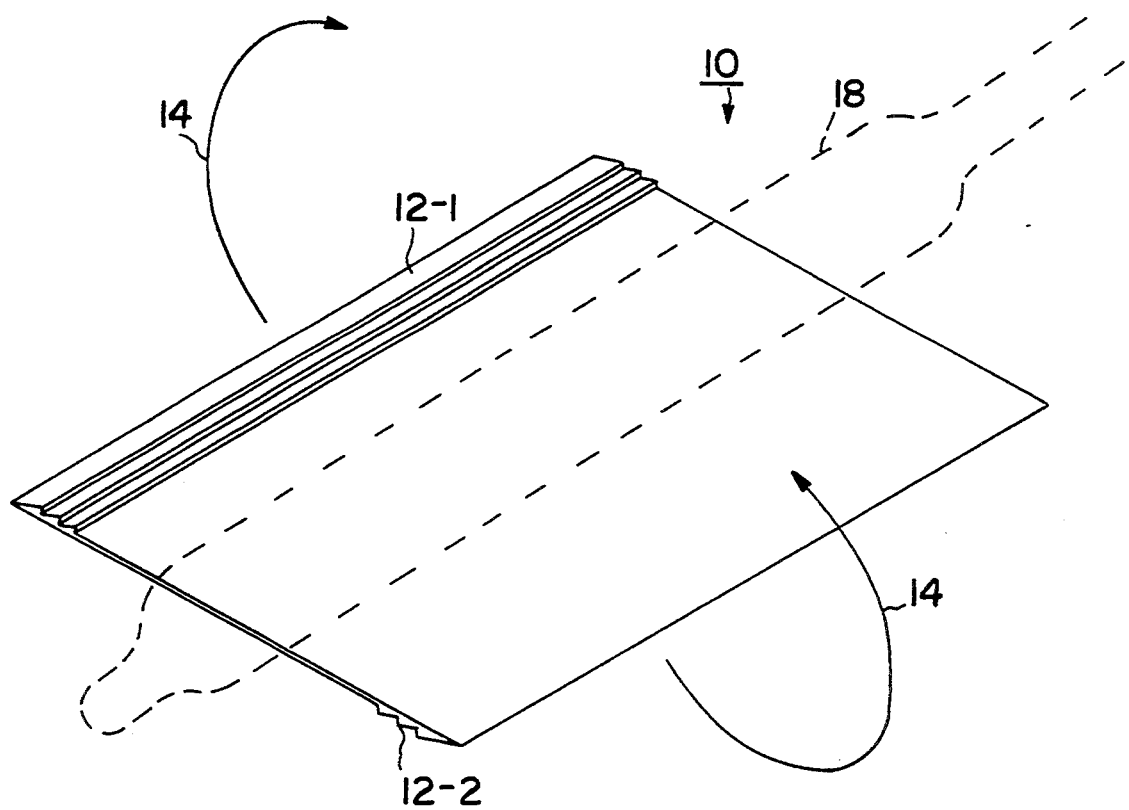
FIG. 1 is an enlarged perspective view of a balloon protector in accordance with one embodiment of the invention in an uncoiled configuration.

Referring to FIG. 1, there is shown a balloon protector 10 in accordance with an illustrative embodiment of the present invention. Balloon protector 10 is shown in FIG. 1 in an uncoiled configuration, i.e., in a substantially planar state. As can be seen from FIG. 1, balloon protector 10 is provided with two sets of angular, longitudinally disposed ribs, designated as 12-1 and 12-2. In particular, ribs 12-1 are disposed on a first planar face of balloon protector 10 along a first edge thereof, while ribs 12-2 are disposed on the opposite planar face of protector 10, and along the opposite edge thereof, with respect to ribs 12-1.

Figure 2:
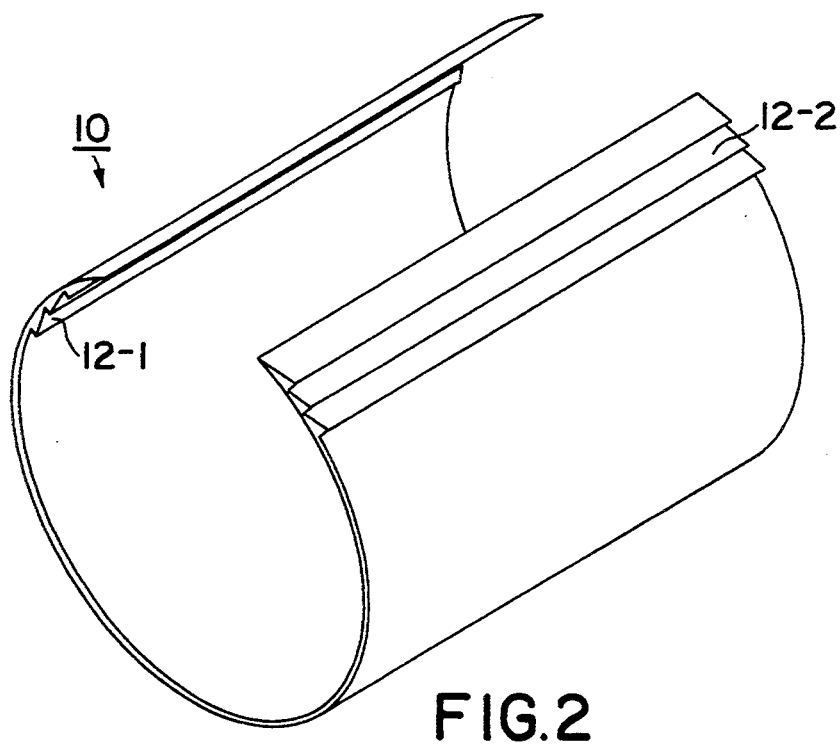
FIG. 2 is an enlarged perspective view of the balloon protector of FIG. 1, shown in the process of being placed into a coiled configuration.

The arrangement of ribs 12-1 and 12-2 on protector 10 can perhaps be better appreciated with reference to FIG. 2, which shows protector 10 in the process of being coiled into a cylindrical configuration. That is, protector 10 in FIG. 1 is coiled in the direction of arrows 14 in FIG. 1 to be brought into the configuration of FIG. 2.

As the coiling of protector 10 continues, ribs 12-1 on one end and one side of protector 10 are brought into contact with and slide across ribs 12-2 on the opposite side and opposite end of protector 10. As shown in the perspective view of FIG. 3, the angularity of ribs 12-1 and 12-2 is such that when protector 10 is coiled into a cylindrical configuration, ribs 12-1 and 12-2 interlock to hold protector 10 in this configuration, a cylinder of predetermined diameter, suitable for covering a balloon or other catheter feature.

Those of ordinary skill in the art will appreciate an advantageous feature of the present invention, namely, that in installing protector 10 over a balloon it is not necessary for protector 10 to be slid over the balloon. Instead, protector 10 may be simply placed over the balloon and coiled or wrapped around the balloon, such that there is no risk of damage to the balloon. This is illustrated in FIG. 1, wherein a balloon 18 shown in phantom is disposed on top of protector 10 prior to protector 10 being coiled or wrapped in the direction of arrows 14 around balloon 18. Protector 10 locked into its cylindrical configuration around balloon 18 is shown in FIG. 5.

Figure 3:
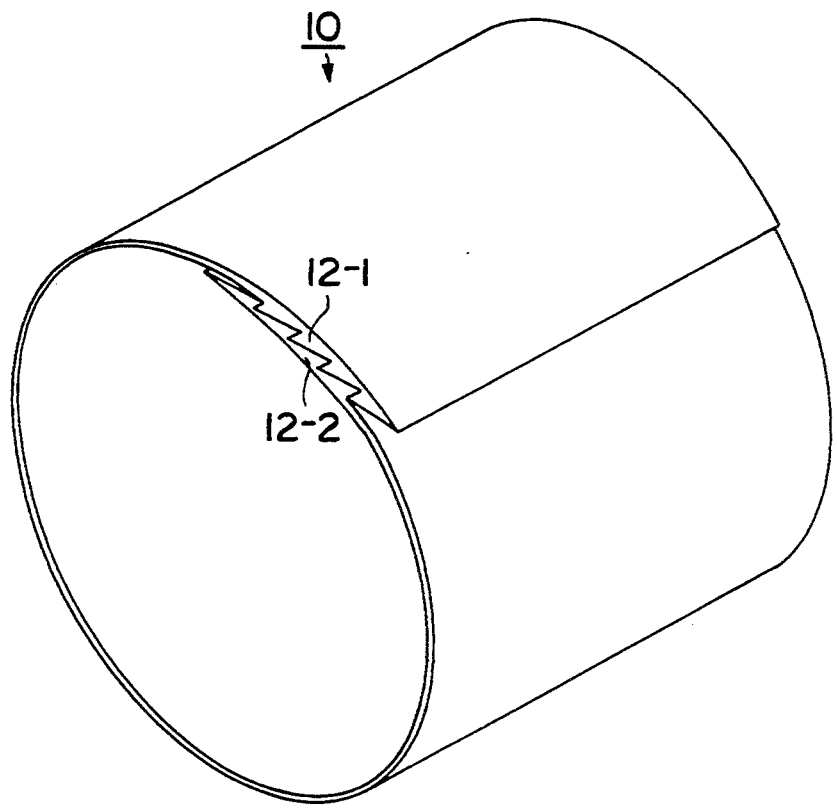
FIG. 3 is an enlarged perspective view of the balloon catheter of FIG. 1, shown in its fully coiled configuration.
Figure 4:
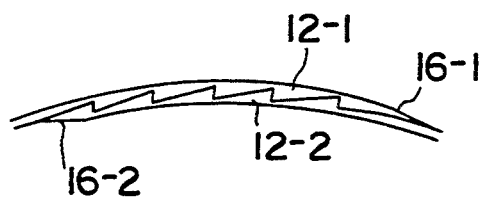
FIG. 4 is an enlarged end view of a portion of the protector of FIG. 1 including the interlocking ends thereof.

When protector 10 is coiled or wrapped into a cylindrical configuration and locked in such position through operation of ribs 12-1 and ribs 12-2, as shown in FIG. 3, the interior surface of protector 10 when locked into its cylindrical configuration is substantially smooth, due to tapers formed in the edges of protector 10 associated with ribs 12-1 and ribs 12-2. This tapering may perhaps be best appreciated with reference to the enlarged end view of ribs 12-1 and ribs 12-2 of FIG. 4, wherein ribs 12-1 and ribs 12-2 are shown in the interlocked state of FIG. 3. Tapers associated with ribs 12-1 and ribs 12-2 are designated in FIG. 4 as 16-1 and 16-2, respectively. The smoothness of the interior surface of protector 10 when protector 10 is in its cylindrical configuration prevents a balloon around which protector 10 may be wrapped from being damaged.

It is contemplated that protector 10 may be made of any number of materials, but it is presently believed that polyethylene or polypropylene have suitable qualities of hardness, elasticity, and sterilizability for the purposes of practicing the present invention. In addition, it is contemplated that protector 10 advantageously may be made either by extrusion or by injection molding, as would be appreciated by those of ordinary skill in the art.

Figure 5:
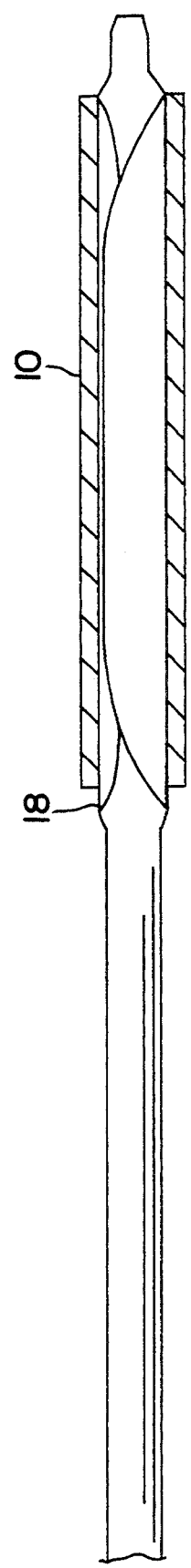
FIG. 5 is a side view of the balloon protector from FIG. 1 installed around the wrapped balloon of a dilatation balloon catheter.

As would be apparent to those of ordinary skill in the art, if protector 10 is made by extrusion, part of the manufacturing process would involve cutting it to the appropriate length so as to cover balloon 18 as depicted in FIG. 5. If protector 10 is made by injection molding, protector 10 could of course be made to the desired length.

From the foregoing detailed description of a specific embodiment of the invention, it should be apparent that a balloon protector for a dilatation balloon catheter or the like has been described. The embodiment described herein is provided with ribs along opposite edges and opposite sides of a substantially planar component, such that when the planar component is coiled or wrapped into a substantially cylindrical configuration, the ribs interlock to hold the protector in that configuration.

Although a particular embodiment of the invention has been described herein in some detail, this has been done for the purposes of illustration only and is not intended to be limiting with regard to the scope of the present invention as defined in the claims. It is contemplated that various substitutions, alterations, and/or modifications, including but not limited to those specifically discussed herein, may be made to the embodiment described herein without departing from the spirit and scope of the present invention, as defined in the appended claims, which follow.

In particular, one variation of the invention that is contemplated is to form protector 10, either by extrusion or injection molding, such that its natural configuration is substantially as shown in FIG. 2, rather than planar as previously described with reference to FIG. 1. It is believed that this may be desirable in order to reduce the amount of force necessary to close protector 10 into its locked, cylindrical position. Nonetheless, if the natural configuration of protector 10 was made to be as shown in FIG. 2, balloon 18 could still be inserted into protector 10 without risk of damage to balloon 18.

Also, while the present invention has been described herein with reference to an embodiment having a plurality of ribs disposed longitudinally along opposing edges of protector 10, it is contemplated that having only a single, longitudinal, angular rib along each edge of protector 10 would be sufficient to enable protector 10 to be coiled or wrapped around balloon 18 and locked into place.

What is claimed is:

1. A combination balloon and balloon protector for a dilatation catheter, comprising:
   a balloon;

a substantially planar, flexible element having first and second opposing planar faces and first and second opposing edges; and the first and second opposing edges being brought into contact with one another and secured to each other such that the planar element is deformed into a cylindrical tube which maintains a tight compressive force about the balloon.

2. A balloon protector in accordance with claim 1, wherein said planar element is made of polyethylene.

3. A balloon protector in accordance with claim 1, wherein said planar element is made of polypropylene.

4. A balloon protector according to claim 1 further comprising:

at least one first longitudinal, angular rib disposed on said first planar face along said first edge;

at least one second longitudinal, angular rib disposed on said second planar face along said second edge; and wherein said at least one first and said at least one second angular ribs are adapted to engage one another when said planar element is rolled into a substantially cylindrical configuration, such that said planar element is thereby maintained in said cylindrical configuration.

5. A method of installing an initially planar balloon protector around a dilatation catheter balloon comprising the steps of:

placing a balloon on a planar face of a balloon protector;

wrapping said balloon protector around said balloon such that opposite edges of said protector are brought into contact;

securing said opposite edges together to hold said protector in a cylindrical configuration around said balloon.

6. A method in accordance with claim 5, wherein said step of securing comprises engaging at least one angular rib disposed along a first edge of a first planar surface of said planar balloon protector with at least one angular rib disposed on a second edge, opposite from said first edge, of a second planar surface, opposite said first planar surface, of said planar balloon protector.

7. A method of installing an initially planar balloon protector around a dilatation catheter balloon comprising the steps of:

providing a balloon;

providing a substantially planar, flexible element having a first and a second opposing planar face and a first and a second opposing edge;

placing said balloon on said first planar surface of said flexible element; bringing said first opposing edge into contact with said second opposing edge; and securing said first and second opposing edges to each other such that the planar element is deformed into a cylindrical tube which maintains a tight compressive force about the balloon.

8. A method according to claim 7 wherein the step of securing comprises:

providing at least one first longitudinal, angular rib disposed on said first planar face along said first edge;

providing at least one second longitudinal, angular rib disposed on said second planar face along said second edge; and providing said at least one first and said at least one second angular ribs which are adapted to engage one another when said planar element is rolled into a substantially cylindrical configuration, such that said planar element is thereby maintained in said cylindrical configuration.

* * * * *